United States Patent [19]
Kwiatkowski et al.

[11] Patent Number: 6,137,009
[45] Date of Patent: Oct. 24, 2000

[54] METHOD OF MANUFACTURING FLUMETRALIN

[75] Inventors: Stefan Kwiatkowski; Steven G. Mobley; Kryzsztof Pupek; Miroslaw Golinski, all of Lexington, Ky.; Paul D. Smith, Seabrook, Tex.

[73] Assignee: SRM Chemical, Ltd. Co., League City, Tex.

[21] Appl. No.: 09/416,543

[22] Filed: Oct. 12, 1999

[51] Int. Cl.$^7$ ................................................. C07C 209/00
[52] U.S. Cl. .............................................................. 564/386
[58] Field of Search ............................................. 564/386

[56] References Cited

U.S. PATENT DOCUMENTS

| | | | |
|---|---|---|---|
| 3,686,230 | 8/1972 | Maravetz | 260/347.7 |
| 4,046,809 | 9/1977 | Wilcox | 260/570.9 |
| 4,169,721 | 10/1979 | Wilcox | 71/121 |

FOREIGN PATENT DOCUMENTS

| | | |
|---|---|---|
| 10561/92 | 1/1992 | Australia . |
| 891327 | 3/1982 | Belgium . |
| 2 128 603 | 5/1984 | United Kingdom . |

OTHER PUBLICATIONS

Emerson, W.S., "The Preparation of Amines by Reductive Alkylation", *Organic Reactions* 4:174–255 (1948).

*Primary Examiner*—Samuel Barts
*Attorney, Agent, or Firm*—Howrey Simon Arnold & White, LLP

[57] ABSTRACT

The invention is a process to manufacture the intermediate secondary amine N-ethyl-2-chloro-6-fluoro-benzylamine, and then the process of reacting this intermediate to manufacture the herbicide flumetralin. Equimolar quantities of monoethylamine, sodium hydroxide, and 2-chloro-6-fluorobenzyl chloride are reacted at a temperature between about 70° C. and about 100° C. in a composition containing at least 2.5 times the required quantity of monoethylamine. The reagent monoethylamine functions as solvent and heat sink for the reaction, and also minimizes the formation of undesired byproducts. The excess monoethylamine is removed after formation of the intermediate. Then, equimolar quantities of sodium hydroxide in water and molten 4-chloro-3-5-dinitrobenzotrifluoride are added to the intermediate, and the temperature is controlled between about 90° C. and about 115° C. The product of this reaction is relatively pure, i.e., 98 percent by weight, molten flumetralin. It is advantageous to wash the product with boiling water to facilitate removal of salt and excess sodium hydroxide.

43 Claims, No Drawings

METHOD OF MANUFACTURING FLUMETRALIN

FIELD OF THE INVENTION

This disclosure involves a method of synthesis of N-alkyl-2-halo-6-halo-benzylamines, more specifically N-ethyl-2-chloro-6-fluoro-benzylamine, and a method of synthesis of N-benzyl-N-alkyl-2,6-dinitro-4-methylaniline compounds, specifically the herbicide flumetralin, N-(2-chloro-6-fluorobenzyl)-N-ethyl-2,6-dinitro-4-trifluoromethyl-aniline.

BACKGROUND OF THE INVENTION

N-benzyl-N-alkyl-2,6-dinitro-4-trifluoromethylaniline compounds have been used as herbicides and as plant control regulators. See, for example, U.S. Pat. No. 4,046,809, which defines a class of these compounds that are useful as plant control regulators. These classes of compounds have also found utilities in other areas, for example as germicides.

A method of manufacturing various N-benzyl-N-alkyl-2,6-dinitro-3-amino-4-trifluoromethylaniline compounds is described in U.S. Pat. No. 4,046,809. The U.S. Pat. No. 4,046,809 method of manufacture involves reacting, for example, substantially equimolar quantities of 2,4-dichloro-3,5-dinitrobenzotrifluoride, N-ethyl-2-chloro-6-fluorobenzylamine, and triethylamine. The resulting compound is then reacted with ammonia or lower alkyl-amino or lower di-alkyl-amino compound to give the desired compound.

The U.S. Pat. No. 4,046,809 method of manufacture requires that all reactants be dissolved in a suitable aprotic solvent, such as tetrahydrofuran, a dioxane, or a low molecular weight ether. The solutions were mixed while the temperature was maintained below 10° C., and placed under nitrogen atmosphere for several days. The trialkylamine is a hydrogen acceptor, and any compound which forms an insoluble precipitate, i.e., benzylamine, pyridines, or alkali metal hydroxides, can be used. The precipitated triethylamine hydrochloride is removed, and the solution is mixed with excess ammonia or the appropriate mono- or di-alkyl-amine at a temperature of –15° C. The solvent is then vaporized or otherwise removed. Problems with this method are the reaction time, the need for a solvent system and the need to separate and recover the solvent.

A method of manufacture described in U.S. Pat. No. 4,169,721 involves reacting substantially equimolar quantities of 4-trifluoromethyl-2,5-dinitro-1-chlorobenzene, a substituted benzylamine or a substituted N-alkylbenzylamine, and a trialkylamine or other acid acceptor such as pyridines, alkylpyridines, metal hydroxides or excess benzylamine. Again, this method of manufacture requires that all reactants be dissolved in a suitable aprotic solvent, such as tetrahydrofuran, a dioxane, or a low molecular weight ether. Again, problems with this method are the reaction time, the need for a solvent system and the need to separate and recover the solvent.

The method of manufacture described in U.S. Pat. No. 4,169,721 does not specifically describe a method for preparing the intermediate benzylamine or N-alkylbenzylamine but refers to literature methods involving reductive alkylation of a benzaldehyde and ammonia or an alkylamine. The use of this type of reaction to manufacture the intermediate secondary amine N-ethyl-2-chloro-6-fluoro-benzylamine (EBA) required in the synthesis of flumetralin is shown below:

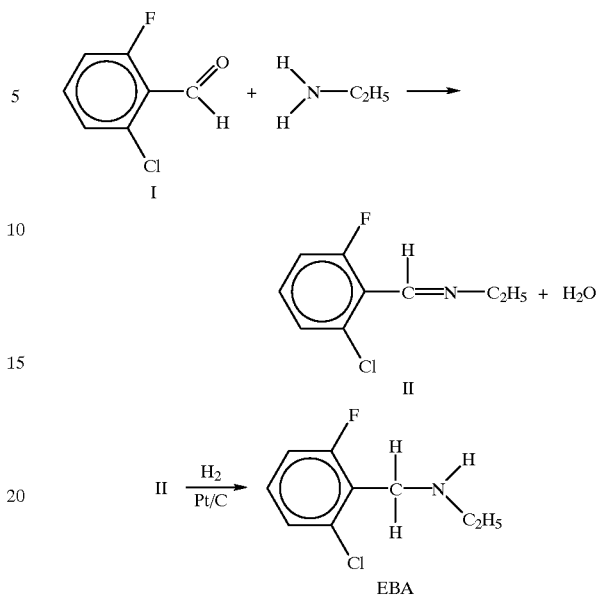

Problems with this U.S. Pat. No. 4,169,721 method of producing the intermediate amine EBA are the formation of significant quantities of four undesired byproducts due to competing reactions of hydrolysis, dehydrohalogenation and dimerisation. The four undesired byproducts produced when following the synthesis proposed in U.S. Pat. No. 4,169,721 are shown below:

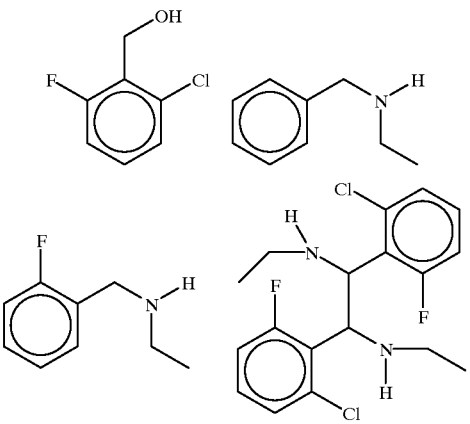

This U.S. Pat. No. 4,169,721 method requires expensive noble metal catalysts and yields significant quantities of undesirable impurities. Gas chromatographic analysis of the reaction mixture obtained by the catalytic reduction of formula II with standard Pt/C catalyst in methanol solvent reveals four separate impurities are present at a combined concentration of approximately 47 weight percent, with a subsequent yield of only 53 weight percent of EBA. Not only would this method require costly separation of the impurities from the desired intermediate, but more importantly, the yield on the expensive starting material is economically unacceptable. The use of sulfided Pt/C catalysts, while reducing the number and quantity of dehalogenated impurities, still resulted in only 63 weight percent EBA, with the remainder being essentially the high molecular weight dimeric impurity shown above.

Great Britain Patent 2,128,603 describes a method of synthesis of N-(dihalobenzyl)-N-alkyl-2,6-dinitro-4- trifluoromethylanilines, and in particular the herbicide flumetralin, via NaBH$_4$ reduction of a Schiff base. The NaBH4 reagent is prohibitively expensive to effect the desired reduction and requires the addition to the process of yet another solvent such as methanol. This method also results in formation of a benzyl alcohol impurity. This process is similar to the reductive alkylation mentioned in U.S. Pat. No. 4,169,721 except it describes reduction of the intermediate imine (Schiff base), structure II above, with NaBH$_4$.

GB 2,128,603 also makes reference to prior art synthesis of EBA involving the catalytic (Pt/C) reductive alkylation of an aldehyde.

The GB 2,128,603 route to the secondary amine EBA is shown below:

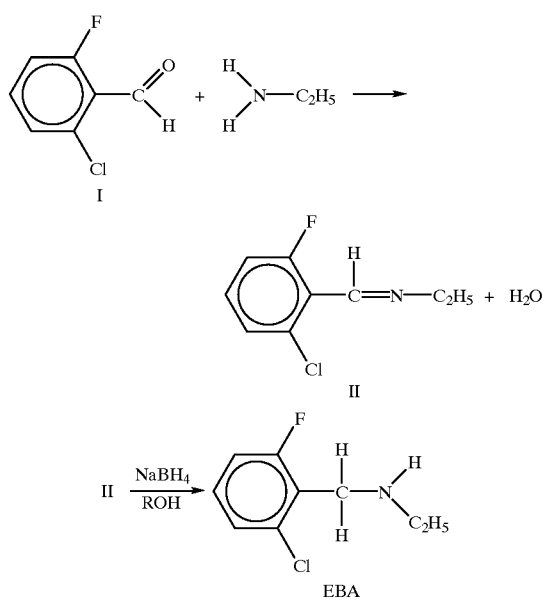

Manufacturing the herbicidal compounds such as flumetralin is a two step process that begins with the synthesis of the intermediate secondary amine. The various proposed methods described above involve producing an intermediate N-alkyl-2-halo-6-halo-benzylamine that in one embodiment contains a —NH—R moiety in the number 1 position. This intermediate compound is then reacted with 4-chloro-3,5-dinitro-benzotrifluoride (DNCB) or similar compound to form the desired herbicidal compounds, liberating a hydrochloric acid molecule.

U.S. Pat. No. 4,169,721 describes the use of triethylamine in tetrahydrofuran to react with the hydrogen chloride formed during the reaction. This introduces another component with safety and environmental concerns and as described would require purification, for example by filtration of the solid ammonium salt and tetrahydrofuran solvent evaporation. The process of GB 2,128,603 is similar in that it uses toluene as the solvent, and an alkali salt as the acid acceptor. The processes of the a) U.S. Pat. No. 4,169,721 and b) GB 2,128,603 are shown below:

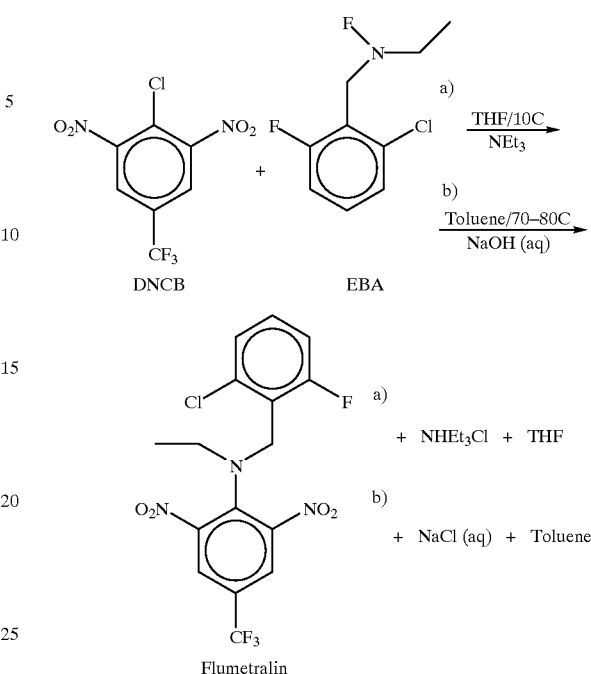

What is needed is a method of manufacturing N-benzyl-N-alkyl-2,6-dinitro-4-trifluoromethylanilines that uses less solvent and less costly reagents, and that has higher yield and less troublesome byproducts.

SUMMARY OF THE INVENTION

The present invention is a process to manufacture the intermediate secondary amines such as N-alkyl-2-halo-6-halo-benzylamines, for example EBA, and also a process to manufacture N-benzyl-N-alkyl-2,6-dinitro-4-trifluoromethylanilines, in particular the herbicide flumetralin, N-(2-chloro-6-fluorobenzyl)-N-ethyl-2,6-dinitro-4-trifluoromethylaniline. Manufacturing the latter class of compounds is a two step process. The first step is the alkylation of an alkyl amine with a benzyl chloride to produce a benzyl amine, for example the intermediate N-alkyl-2-halo-6-halo-benzyl-amine. Step 2 involves the reaction of the benzyl amine with a dinitroaryl chloride to yield the desired compounds. For example, this intermediate compound EBA is then reacted with 4-chloro-3,5-dinitro-benzotrifluoride or similar compound to form the desired herbicidal N-benzyl-N-alkyl-2,6-dinitro-4-trifluoromethyl-aniline compounds.

The synthesis of benzyl amines, particularly N-alkyl-2-halo-6-halo-benzylamines, for example EBA, by the present invention begins by reacting a composition containing monoethylamine (MEA), an alkali metal hydroxide such as sodium hydroxide, and a benzyl chloride, for example 2-chloro-6-fluorobenzyl chloride (CFBC). The composition should contain CFBC to MEA in the molar ratio between about 1:2.5 to as high as desired, for example about 1:20, most preferably between about 1:4 and about 1:6. In the present invention, MEA functions as reagent, solvent, proton acceptor and heat sink for the reaction. Excess MEA also minimizes the formation of undesired byproducts. The sodium hydroxide functions as the ultimate proton acceptor by converting to the free-base any protonated monoethylamine.

The MEA and sodium hydroxide are typically available as solutions in water, and use of these solutions is preferred.

However, anhydrous MEA and solid sodium hydroxide may also be used. The temperature is preferably kept between about −5° C. and about 25° C. during the mixing of the composition, but is then increased to preferably between about 70° C. and about 100° C. for the reaction to proceed. As the reaction proceeds, a separate water-rich phase will form. Sodium chloride will also form.

The excess MEA is beneficially removed from the composition after formation of EBA, typically as a vapor. Though not necessary, the water can be decanted off, and additional water washes can be done to remove salt. The resulting intermediate secondary amine, EBA, is at high purity and therefore can be used without subsequent purification.

The temperature of the intermediate EBA from the first step is then adjusted preferably between about 90° C. and about 95° C. Then solid sodium hydroxide or a solution of caustic, i.e., 50 percent by weight sodium hydroxide in water, and molten 4-chloro-3-5-dinitrobenzotrifluoride are added to the EBA. The addition of sodium hydroxide and molten 4-chloro-3-5-dinitrobenzotrifluoride is advantageously controlled so that the temperature of the reaction composition remains between about 103° C. and about 115° C. If the flumetralin is being manufactured in a batch reactor, it is preferred that the sodium hydroxide and the molten 4-chloro-3-5-dinitrobenzotrifluoride be added in parallel in a controlled manner. The addition of the compounds is such that approximately equimolar quantities of sodium hydroxide, EBA, and 4-chloro-3-5-dinitrobenzotrifluoride are added to the reaction vessel over the course of the reaction.

The reactants should be allowed to react for a time sufficient to reach the desired conversion, i.e., at least about a minute, and preferably about one half hour or more to ensure complete conversion. The product of this reaction is relatively pure, that is, greater than about 95 percent by weight, preferably greater than about 98 percent by weight, of molten flumetralin. It is advantageous to wash the product with boiling water to facilitate removal of salt and excess sodium hydroxide and any other water-soluble impurities. The water is immiscible with the product, and is therefore easily decanted away.

After cooling, the product of the reaction described above forms large orange crystals with a melting point of about 100° C. to 103° C.

DETAILED DESCRIPTION OF THE INVENTION

The invention is a process to manufacture an intermediate secondary benzylamine, for example EBA, and then to manufacture N-benzyl-2,6-dinitro-4-trifluoromethylanilines, in particular the herbicide flumetralin, N-(2-chloro-6-fluorobenzyl)-N-ethyl-2,6-dinitro-4-trifluoromethylaniline. The applicability of the process to the manufacture of other dinitroaniline herbicides such as trifluralin, benfluralin, ethalfluralin, fluchloralin and prodiamine, which contain N-alkyl substituents other than benzyl, will be immediately apparent.

The synthesis of EBA requires reacting a composition containing MEA, an alkali such as sodium hydroxide, and CFBC:

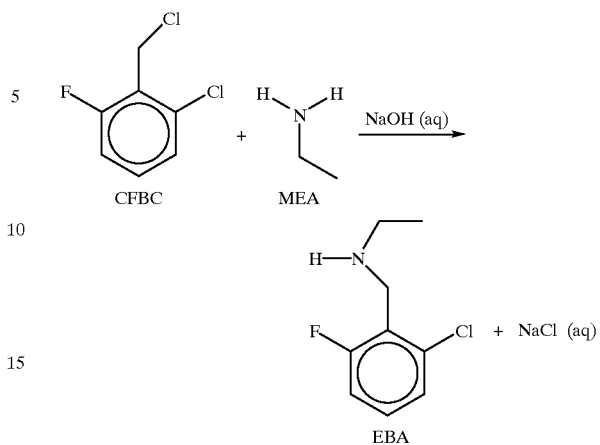

The equivalent molar ratio of CFBC to alkali, i.e., sodium hydroxide in the composition is between about 1:0.7 to about 1:1.4, preferably between about 1:0.9 to about 1:1.2, more preferably between about 1:1 to about 1:1.1. A small excess of sodium hydroxide or other base is beneficial.

It is recognized that certain reactions may occur on admixing the reactants, even at a reduced temperature. It is also recognized that admixing can occur at various rates, and in various sequences. The compositions and mole ratios as used herein are meant to encompass the totality of reactants added to a composition.

The alkylation of amines and can be depicted as follows:

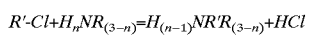

Where the R substituents are alkyl groups and n=0,1,2 or 3. In the case of n=0, a quaternary ammonium salt is formed, i.e. R'NR3+Cl—. A problem with this method of synthesizing substituted amines is that as the reaction progresses, the product amine can compete with the reactant amine yielding side products with a higher degree of substitution than is desired. The amount of the more highly substituted product can be suppressed by the addition of excess reactant amine, i.e. in the present invention, MEA.

The molar ratio of CFBC to MEA in the reaction is 1:1. This is not the desired ratio in the composition, however, because in the absence of excess MEA other solvents are needed, and undesired byproducts form in greater concentrations.

The composition should contain CFBC to MEA in the molar range between about 1:2.5 to as high as desired, for example about 1:20. The molar ratio of CFBC to MEA is preferably between about 1:2.7 and about 1:12, more preferably between about 1:3 and about 1:10, even more preferably between about 1:4 and about 1:8, and most preferably between about 1:4 and about 1:6. While added benefits, i.e., lower quantities of byproducts, accrue with addition of more MEA, this reactant/solvent must be recovered and reused, so the upper limit reflects practical concerns such as reactor volume and the costs of recovering the excess MEA.

The MEA is typically available as anhydrous or as 70 percent in water. Either form is useful in this process. For ease in handling, and because the presence of water is not detrimental to the reaction, the 70 percent MEA in water is preferred.

Similarly, the form of alkali is not overly important. Any soluble alkaline metal hydroxide, i.e., sodium hydroxide or potassium hydroxide, or alkaline earth hydroxide, or oxide that forms the hydroxide, can be used. Other strong bases, for example sodium methoxide, are also operable.

Generally, sodium hydroxide or lye is selected based on cost, availability, and concentration. It is preferred that the alkali be dissolved or partially dissolved to facilitate mass transfer, and the solubility of alkaline earth hydroxides, i.e., calcium hydroxide, is limited. Typically, sodium hydroxide is commercially available in aqueous form at concentrations of between about 10% and about 50% by weight in water. Again, because the 50% by weight solution is generally the least costly and will save reactor volume, this solution is preferred. Solid sodium hydroxide may also be used. Combinations of solid and dissolved alkaline metal hydroxides, alkaline earth hydroxides, and alkaline earth oxides may be used. It is important that the alkali or alkaline earth base, and not the MEA, be the ultimate receptor of the hydrogen created during the reaction.

It is preferred that the reactants and the reaction mixture be between about −5° C. and about 25° C., preferably between about 0° C. and about 15° C., during the admixing of the reaction composition. Exothermic reactions generally require some mechanism for heat removal, for example by cooling coils or an ice bath. It may be advantageous to, for example, add ice to the reaction composition to control temperature during admixing. For batch reactors, it is advisable to add the ingredients at slow, controlled rates so that temperature control can be maintained.

The reactants admixed in the stated ratio need no additional solvent. While solvent can be added, the solvent serves no significant utility, occupies reactor space, and requires additional separation and purification.

The temperature of the reaction composition is then increased to between about 70° C. and 120° C., preferably between about 75° C. and 110° C., more preferably between about 80° C. and about 100° C., most preferably between about 80° C. and about 90° C.

During the reaction, a separate EBA-rich phase and a separate water-rich phase will form. The salt, i.e., sodium chloride if sodium hydroxide is used as the base, will also form. Depending on the amount of water in the reactants, there may be too much salt to dissolve in the water-rich phase, and solid salt crystals may form.

This method of synthesizing EBA has several advantages when incorporated into the overall synthesis of flumetralin. Firstly, the reagent MEA functions as a reactant, solvent and heat sink for the reaction. Therefore, unlike prior art methodology, the introduction of additional components as solvent, and the subsequent need to remove and recover these solvents, is not necessary.

Secondly, the excess MEA serves to suppress formation of the only side product, the tertiary amine, N,N-di-(2-chloro-6-fluorobenzyl)-N-ethylamine (DBA), shown below. This method for synthesizing EBA, via the amination of 2-chloro-6-fluorobenzylchloride, yields only this one impurity in any significant quantity. Moreover, by increasing the excess of MEA used in the reaction, the concentration of this impurity can be reduced.

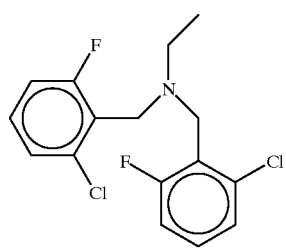

DBA

Table 1 demonstrates this effect by comparing yields of the present invention in which the molar ratio of MEA to 2-chloro-6-fluorobenzylchloride was varied from 2.4:1 to 15.8:1. $^1$H-NMR analysis of the resulting reaction mixture confirmed that concentration of the tertiary amine byproduct relative to the desired secondary amine intermediate EBA had decreased from 7.9 to 0.5 mole percent. Following the preferred procedure, the concentration of the undesired tertiary amine in EBA is less than 3 mole percent and it is the only detectable impurity.

TABLE 1

Effect of MEA to CFBC Ratio on Byproduct DBA Formation

| Run# | 1 | 2 | 3 | 4 | 5 |
| --- | --- | --- | --- | --- | --- |
| Moles MEA/moles CFBC | 2.37 | 3.16 | 4.74 | 6.32 | 15.3 |
| Moles EBA/moles DBA | 12 | 21 | 49 | 71 | 200 |
| Mole % DBA in EBA | 7.9 | 4.5 | 2.0 | 1.4 | 0.5 |
| Weight % DBA in EBA | 13.1 | 7.7 | 3.5 | 2.4 | 0.9 |

Minimizing the formation of DBA is critical to production economics of flumetralin for two reasons. It increases the yield of EBA relative to the expensive feedstock, CFBC, as shown by the type and relative amounts impurities found in the present process compared to prior art processes. Also, it permits the use of crude EBA directly in subsequent processing steps without the expense of intermediate purification. Any DBA present in EBA will carry through to the final product. A four-fold molar excess of MEA (volume ratio of about 2.67 to 1) is sufficient to limit the concentration of DBA in the flumetralin at less than 1 weight percent.

The excess MEA is beneficially removed from the composition after formation of EBA. The reaction temperature is typically about 80° C. Anhydrous mono-ethylamine boils at about 17° C. and the monohydrate boils at 38° C. The reaction is therefore usually performed under pressure once the reaction composition is heated. This tendency to vaporize is advantageous. Venting the reactor to atmospheric pressure will effectively remove MEA as a vapor. Imposing a vacuum, such as between about 40 mm to about 300 mm of mercury, will ensure rapid and quantitative removal of un-reacted MEA from the reaction composition. Complete removal of MEA from EBA is critical, as any MEA present in the subsequent reaction of EBA with DNCB will lead to a competitive substitution reaction. It is therefore desirable to reduce the concentration of MEA in the EBA to below about 2%, preferably below about 0.5%, even more preferably below about 0.1%, and most preferably below about 0.01%, by weight.

The temperature and vacuum conditions can be selected to boil water. The water present from the MEA, sodium hydroxide, and other sources, if any, will form a separate phase. There will often be salt, for example sodium chloride, present in quantities that exceed the solubility in the aqueous phase. Indeed, if the alkali is dissolved in another solvent, for example methanol, or if the alkali is introduced as a solid or a mixture of solid and solution, and if anhydrous MEA is used, there may be almost no aqueous phase present.

The salt can be separated from the EBA by, for example, filtration or centrifugation. This is not preferred because, generally, an aqueous phase is present. Adding water dissolves salt, and the salt can then be removed from the EBA by separating the immiscible EBA from the brine. The amount of water added should be such that the resulting brine solution is nearly saturated, thereby maximizing the density difference between the layers to insure rapid layer separation. Additional water washes can be employed to remove residual traces of salt.

The residual water, MEA, and traces of other solvents if any, can be removed from the reactor by exerting the previously described vacuum. MEA is beneficially recovered from the vapor by condensation or by absorption in, for example, water. It is generally not necessary to remove all the water from the reactor, especially since the water typically contains a small excess of caustic or brine, both of which are present in subsequent reactions.

The oily liquid upper layer contains the intermediate secondary amine, EBA, at a high purity, i.e., greater than 95 mole percent. This material can be used without purification.

The above-described method for the synthesis of EBA is superior to those described in the prior art such as Great Britain Patent 2,128,603, which requires the use of an expensive reagent, $NaBH_4$ and separate solvent systems (alcohol, methylene chloride). This prior art method also suffers from the tendency to hydrolyze the C=N bond resulting in the byproduct benzyl alcohol. Lastly, the Great Britain Patent 2,128,603 identified the problems associated with the previously reported literature methods (see W. S. Emerson, *Organic Reactions,* 4, p174, 1948) of catalytic reductive alkylation with Pt,Pd/C catalysts to produce EBA, namely hydrogenolysis of the C=N bond, dehalogenation of the aromatic ring and the expense of noble metal catalysts. None of these disadvantages are present in the currently described system.

The current invention also has numerous advantages over the prior art in the second step of the process, namely the reaction of EBA with 4-chloro-3,5-dinitro-benzotrifluoride (DNCB) to form flumetralin.

One advantage of step number 2 of the current invention is attributed to the absence of process solvent. The absence of solvent is critical to production economics as it eliminates the expense of separation, purification and recycling of the solvent itself while maximizing the space-time yield of the reactor.

Additionally, the use of a caustic such as sodium hydroxide to neutralize the hydrochloric acid formed during the reaction is the preferred method of our invention as the resulting byproduct, i.e., salt, can be removed from the reaction by layer separation and decantation after dilution with the appropriate quantity of water. The presence of excess sodium hydroxide during Step 2 has the additional benefit of inhibiting the formation of N-nitrosamines that can result from nitrogenous impurities present in DNCB.

In Step 2 of the current invention, the temperature of the EBA formed in Step 1 is adjusted as needed to between about 80° C. to 105° C., preferably between about 85° C. and 100° C., more preferably between about 90° C. and about 95° C. Then caustic and molten, that is, at greater than about 85° C., 4-chloro-3-5-dinitrobenzotrifluoride (DNCB) are added to the EBA.

The caustic can be an alkali metal hydroxide, for example sodium hydroxide, or an alkaline earth hydroxide, or an oxide that forms hydroxides. Again, generally a 50 percent by weight sodium hydroxide in water is the preferred caustic, because it is relatively inexpensive, is in solution, and easy to handle. Solid sodium hydroxide may also be used.

The addition of sodium hydroxide and DNCB is advantageously controlled so that the temperature of the reaction composition remains between about 80° C. and about 130° C., preferably between about 95° C. and about 120° C., more preferably between about 103° C. and about 115° C. This control will typically involve cooling, as the formation of flumetralin is exothermic. The reaction is shown below:

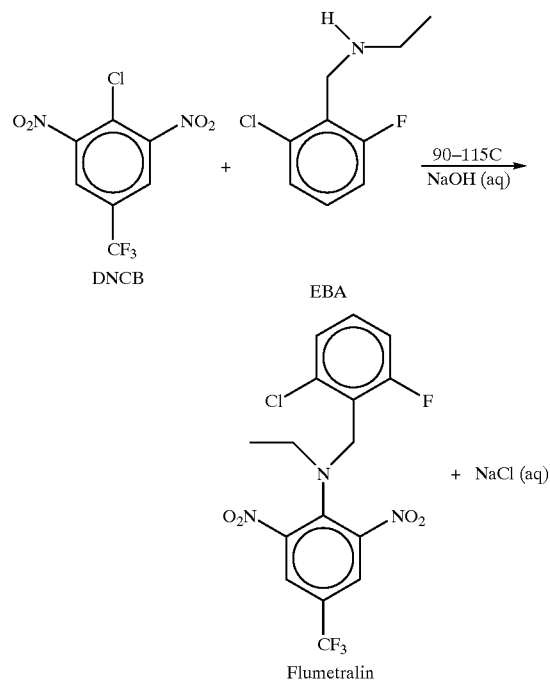

If the flumetralin is being manufactured in a batch reactor, it is preferred that the sodium hydroxide and the molten DNCB be added in parallel in a controlled manner.

The sequence of addition is not particularly important. Sequential addition of EBA and aqueous sodium hydroxide to molten DNCB under the reaction conditions described above yielded similar results. The addition of a pre-mixed solution of EBA and aqueous sodium hydroxide to molten DNCB under the reaction conditions described above also yielded similar results. There are an infinite number of combinations and ratios in which the materials may be added. However, contact of EBA with DNCB (potentially containing trace amounts of nitrosating agents) in the absence of sodium hydroxide should be avoided to prevent formation of the undesirable N-nitroso derivative of EBA. Also, contact of sodium hydroxide with molten DNCB under the reaction conditions described above in the absence of EBA caused significant hydrolysis of DNCB to the corresponding phenol, and is not a preferred embodiment.

The addition of the compounds is such that approximately equimolar quantities, i.e., within a mole ratio of about 0.95:1 to about 1.05:1 of EBA to DNCB are added to the reaction vessel over the course of the reaction. This same molar ratio is applicable to the alkali metal hydroxide to the DNCB. Generally, a small excess of sodium hydroxide has the additional benefit of inhibiting the formation of N-nitrosamines that can result from nitrogenous impurities present in DNCB. Therefore, the final composition preferably had a mole ratio of about 1.05:1 to about 1:1 of alkali metal hydroxide to the DNCB. Of course, impurities in the reactants, for example the tertiary amine in the EBA, are not reactants.

The reaction composition should be held at temperature for a sufficient time for the reaction to proceed to completion. This time will vary with temperature and with efficiency of mixing. Generally, if the reaction composition is well mixed, and the temperature is between about 105° C. and 115° C., one half hour of additional reaction time is recommended after all reactants are added.

Generally, the product of this reaction is relatively pure, that is, greater than about 95 percent by weight, preferably greater than about 98 percent by weight, of molten flumetralin. As the reaction nears completion, heating may be necessary to insure that the temperature of the reaction composition does not fall below about 105° C., since the melting point of the finished composition is typically between about 100° C. to 103° C. If the reaction temperature drops significantly below 105° C., say about 90° C., the reaction composition may thicken, making mixing difficult.

Unlike prior art methods, in our preferred embodiment no solvents, i.e., toluene or tetrahydrofuran, are present in the reaction mass. The product remains fluid because the temperature is held at or above the melting point temperature of the composition. There is therefore no need to separate out and recover said petroleum solvents.

It is advantageous to wash the product with boiling water to facilitate removal of salt, excess sodium hydroxide and any other water-soluble impurities. Water will typically be present in the reactor, coming from the added aqueous solution of sodium hydroxide. This water can be decanted off prior to washing. A small amount of pressure may of course be needed if the temperature of the composition is held above 100° C. Generally, one to three water washings are sufficient to remove salt. The water is immiscible with the product, and is therefore easily decanted away.

After cooling, the product of the reaction described above forms large orange crystals with a melting point of about 100° C. to 103° C. The molten flumetralin can be transferred to other processes, where it is generally cooled into a solid mass, pellets or powders, and/or admixed with other adjuvants, or other processes known to the art, to make a commercial product.

Finally, it should be noted that U.S. Pat. No. 4,169,721 prior art methodology requires isolation and recrystallization of the crude flumetralin from yet another solvent, i.e., petroleum ether, to achieve the required purity whereas product by our preferred method does not require further purification.

The above described Step 2 process is superior to prior art methods of manufacture because the prior art methods use solvent systems, for example aromatic hydrocarbon and/or tetrahydrofuran, which require purification, handling precautions and add significantly to raw material and processing costs. The absence of solvent is critical to production economics as it eliminates the expense of separation, purification and recycling of the solvent itself while maximizing the space-time yield of the reactor. A comparison of the Great Britain patent 2,128,603 method shows the method of the prior art would yield 0.46 kg of product per liter of reactant volume, whereas the herein described method yields typically greater than 0.6, and typically about 0.77 kg of EBA per liter of reactant volume. Since both methods require similar batch times, our above-described method is capable of producing 67% more flumetralin per unit time in a given reactor compared to the prior art method.

Secondly, the prior art as described in U.S. Pat. No. 4,169,721 describes the use of triethylamine in tetrahydrofuran to react with the hydrogen chloride formed during synthesis of flumetralin. This introduces yet another component with safety and environmental concerns and as described would require filtration of the solid salt and solvent evaporation. The use of sodium hydroxide to neutralize the hydrogen chloride formed during the reaction is the preferred method of our invention as it can be removed from the reaction by layer separation and decantation after dilution with the appropriate quantity of water. The presence of excess sodium hydroxide during this second step has the additional benefit of inhibiting the formation of N-nitrosamines that can result from nitrogenous impurities present in the reactants.

EXAMPLES

Example 1

Example 1 provides one process for the synthesis of N-ethyl-2-chloro-6-fluoro-benzylamine (EBA).

A 22 L round bottom flask equipped with a reflux condenser, stirrer and dropping funnel was placed in an ice-water bath and charged with 12.0 L (9.522 Kg, 148.29 moles) of 70 percent by weight MEA, balance water. Agitation was initiated and the contents cooled to 5° C. Then, 2.0 L (3.03 Kg, 37.87 moles) of 50 percent by weight sodium hydroxide, balance water, was then added dropwise to the MEA solution over a period of approximately 15 minutes in a controlled manner such that the temperature of the mixture stayed below 15° C. A total of 4.5 L (6.445 Kg, 36.0 moles) of CFBC was then added dropwise to the aqueous MEA and sodium hydroxide mixture over a one hour period such that the temperature of the reaction mixture remained below 17° C. The resulting composition was mixed.

The temperature of the water bath was then increased to 80° C. A vacuum of about of 100 mm. mercury was applied and the excess MEA was removed as vapor. The distillation was continued until the distillate began to distill as two phases.

At this point the reaction mixture appeared to be three distinct phases; an organic product liquid phase, an aqueous brine liquid phase and sodium chloride as a finely divided solid suspension. Approximately 5.0 L of de-ionized water was then added to dissolve the solid sodium chloride and generate a two-phase system of which the lower layer was brine and the upper layer contained the desired product. The lower brine layer was then removed.

The oily liquid upper layer was determined to contain 6.383 Kg of the intermediate secondary amine, N-ethyl-2-chloro-6-fluoro-benzylamine (EBA) at a purity of 97.22% as determined by $H^1$-NMR. The overall yield based on the CFBC charge was 94.4%. This material was used further in Example 2 without purification.

Example 2

Example 2 provides one process for the synthesis of flumetralin from the N-ethyl-2-chloro-6-fluoro-benzylamine (EBA).

A total of 6.064 Kg (32.32 moles) of the EBA from Step 1 was reintroduced into the 22 L reactor described above and heated to 90° C. The parallel addition of 2.585 Kg (1.7 L, 32.32 moles) of 50 percent by weight sodium hydroxide, balance water, and molten, that is, at greater than about 85° C., 4-chloro-3-5-dinitrobenzotrifluoride (DNCB) was then initiated. The rate of sodium hydroxide and DNCB was maintained at such a rate that the reactor cooling allowed the temperature of the reaction mixture to be controlled between about 110° C. to 115° C. A total of 2.5 hours was required to complete the addition. The mixture was held at 110° C. for an additional 0.5 hours to complete the reaction.

The reaction mixture was then analyzed for the presence of starting materials (EBA and DNCB) and the pH of the aqueous brine layer was measured and adjusted to 9.5 by adding aqueous sodium hydroxide. In this example, DNCB was detected and an additional 0.151 Kg (0.80 moles) of EBA were added and the mixture was allowed to react for an additional 15 minutes at 110° C. Subsequent analysis confirmed absence of, and therefore presumably complete reaction of, both starting materials.

Approximately 5.0 L of boiling water were then added and the mixture stirred vigorously at 110° C. for 0.5 hours. The phases were allowed to separate and the aqueous layer was removed. The lower product layer was washed again with an additional 5.0 L of boiling water. The phases were again allowed to separate.

The lower product phase contained 13.42 Kg of flumetralin (98.4% yield) at a purity of approximately 98%. After cooling, the product formed large orange crystals with a melting point of about 100° C. to 103° C.

What is claimed is:

1. A process of manufacturing N-alkyl-2-halo-6-halo-benzylamine, said process comprising:
   admixing a monoalkylamine, an alkali, and 2-halo-6-halo-benzyl halide into a reaction composition, wherein the molar ratio of the monoalkylamine to the 2-halo-6-halo-benzyl halide in the reaction composition is at least about 2.5:1, and wherein the molar equivalent ratio of the alkali to the 2-halo-6-halo-benzyl halide in the reaction composition is between about 0.7:1 to about 1.4:1; and
   reacting the composition at a reaction temperature between about 50° C. and about 120° C., thereby forming the N-alkyl-2-halo-6-halo-benzylamine and a salt.

2. The process of claim 1 wherein the monoalkylamine is monoethylamine.

3. The process of claim 1 wherein the 2-halo-6-halo-benzyl halide is 2-chloro-6-fluorobenzyl chloride.

4. The process of claim 1 wherein the alkali is an aqueous solution of an alkaline metal hydroxide.

5. The process of claim 1 wherein the alkali is a solid alkaline metal hydroxide.

6. The process of claim 4 wherein the alkaline metal hydroxide is sodium hydroxide.

7. The process of claim 5 wherein the solid alkaline metal hydroxide is sodium hydroxide.

8. A process of manufacturing N-ethyl-2-chloro-6-fluoro-benzylamine, said process comprising:
   admixing monoethylamine, an aqueous solution of alkali metal hydroxide, and 2-chloro-6-fluorobenzyl chloride into a reaction composition, wherein the molar ratio of the monoalkylamine to the 2-chloro-6-fluorobenzyl chloride in the reaction composition is at least about 2.5:1, and wherein the molar ratio of the alkali metal hydroxide to the 2-chloro-6-fluorobenzyl chloride in the reaction composition is between about 0.7:1 to about 1.4:1; and
   reacting the composition at a reaction temperature between about 50° C. and about 120° C., thereby forming the N-ethyl-2-chloro-6-fluoro-benzylamine and a salt.

9. The process of claim 8 wherein the molar ratio of monoethylamine to 2-chloro-6-fluorobenzyl chloride is at least about 3:1.

10. The process of claim 8 wherein the molar ratio of monoethylamine to 2-chloro-6-fluorobenzyl chloride is at least about 4:1.

11. The process of claim 8 wherein the molar ratio of monoethylamine to 2-chloro-6-fluorobenzyl chloride is at least about 5:1.

12. The process of claim 8 wherein the molar ratio of monoethylamine to 2-chloro-6-fluorobenzyl chloride is at least about 4:1 and about 8:1. 2.

13. The process of claim 8 further comprising controlling the temperature of the reaction composition during the admixing of reagents to between about –5° C. and about 25° C.

14. The process of claim 8 wherein the reaction temperature is between about 80° C. and about 100° C.

15. The process of claim 10 wherein the molar ratio of the sodium hydroxide to the 2-chloro-6-fluorobenzyl chloride in the reaction composition is between about 0.9:1 to about 1.2:1.

16. The process of claim 8 further comprising washing the N-ethyl-2-chloro-6-fluoro-benzylamine with water, wherein the water dissolves salt in the N-ethyl-2-chloro-6-fluoro-benzylamine, and then decanting the water and dissolved salt, thereby removing salt.

17. The process of claim 10 further comprising removing monoethylamine remaining after the reaction from the N-ethyl-2-chloro-6-fluoro-benzylamine, such that the quantity of monoethylamine remaining in the N-ethyl-2-chloro-6-fluoro-benzylamine is below about 0.1 weight percent.

18. The process of claim 17 wherein the monoethylamine is removed as a vapor, further comprising recovering the removed monoethylamine.

19. A process of manufacturing flumetralin, said process comprising:
   admixing N-ethyl-2-chloro-6-fluoro-benzylamine, an alkali, and molten 4-chloro-3-5-dinitrobenzotrifluoride to form a reaction composition, wherein the temperature of the reaction composition is between about 80° C. to 120° C.; and
   reacting the composition to form a product comprising flumetralin in a fluid phase and salt.

20. The process of claim 19 wherein the temperature of the reaction composition is between about 100° C. and about 115° C.

21. The process of claim 19 wherein the alkali comprises aqueous sodium hydroxide in water.

22. The process of claim 19 wherein the alkali comprises solid sodium hydroxide.

23. The process of claim 19 wherein the admixing comprises adding molten 4-chloro-3-5-dinitrobenzotrifluoride to a composition containing N-ethyl-2-chloro-6-fluoro-benzylamine and alkali.

24. The process of claim 19 wherein the admixing consists essentially of adding molten 4-chloro-3-5-dinitrobenzotrifluoride and aqueous solution or a solid composition of sodium hydroxide to a composition containing N-ethyl-2-chloro-6-fluoro-benzylamine.

25. The process of claim 19 wherein the molar ratio of N-ethyl-2-chloro-6-fluoro-benzylamine to 4-chloro-3-5-dinitrobenzotrifluoride is between about 0.95:1 to about 1.05:1, and wherein the molar equivalent ratio of alkali to 4-chloro-3-5-dinitrobenzotrifluoride is between about 0.95:1 to about 1.05:1.

26. The process of claim 25 further comprising washing the molten flumetralin with water to remove salt.

27. The process of claim 19 wherein the N-ethyl-2-chloro-6-fluoro-benzylamine was provided by the process of claim 18.

28. A process of manufacturing flumetralin, said process comprising:
  admixing monoethylamine, a first alkali, and 2-chloro-6-fluorobenzyl chloride into a first reaction composition, wherein the molar ratio of the monoethylamine to the 2-chloro-6-fluorobenzyl chloride in the first reaction composition is at least about 2.5:1, and wherein the equivalent molar ratio of the alkali to the 2-chloro-6-fluorobenzyl chloride in the first reaction composition is between about 0.7:1 to about 1.4:1;
  reacting the first reaction composition at a reaction temperature between about 50° C. and about 120° C., thereby forming N-ethyl-2-chloro-6-fluoro-benzylamine and a salt;
  removing monoethylamine from said first reaction composition, such that the concentration of monoethylamine in N-ethyl-2-chloro-6-fluoro-benzylamine is less than about 2 weight percent;
  admixing the N-ethyl-2-chloro-6-fluoro-benzylamine, a second alkali, and molten 4-chloro-3-5-dinitrobenzotrifluoride to form a second reaction composition, wherein the temperature of the reaction composition is between about 80° C. to 120° C.; and
  reacting the second reaction composition to form a product comprising flumetralin in a fluid phase and salt.

29. The process of claim 28 wherein the first alkali and wherein the second alkali are aqueous solutions or solid compositions of an alkaline metal hydroxide, an alkaline earth metal hydroxide, or a mixture thereof.

30. The process of claim 28 wherein the molar ratio of 2-chloro-6-fluorobenzyl chloride to monoethylamine is at least about 1:3.

31. The process of claim 28 wherein the molar ratio of 2-chloro-6-fluorobenzyl chloride to monoethylamine is at least about 1:4.

32. The process of claim 28 wherein the molar ratio of 2-chloro-6-fluorobenzyl chloride to monoethylamine is at least about 1:5.

33. The process of claim 28 wherein the molar ratio of 2-chloro-6-fluorobenzyl chloride to monoethylamine is at least about 1:2.7.

34. The process of claim 28 wherein the concentration of monoethylamine in N-ethyl-2-chloro-6-fluoro-benzylamine prior to forming the second reaction composition is less than about 0.5 weight percent.

35. The process of claim 28 wherein the concentration of monoethylamine in N-ethyl-2-chloro-6-fluoro-benzylamine prior to forming the second reaction composition is less than about 0.1 weight percent.

36. The process of claim 28 wherein the concentration of monoethylamine in N-ethyl-2-chloro-6-fluoro-benzylamine prior to forming the second reaction composition is less than about 0.01 weight percent.

37. The process of claim 33 wherein the monoethylamine is removed as a vapor, further comprising recovering the removed monoethylamine.

38. The process of claim 28 wherein the temperature of the second reaction composition is between about 100° C. and about 115° C.

39. The process of claim 28 further comprising washing the N-ethyl-2-chloro-6-fluoro-benzylamine with water, separating and decanting the water, thereby removing salt from the N-ethyl-2-chloro-6-fluoro-benzylamine.

40. The process of claim 28 further comprising washing the flumetralin with water, separating and decanting the water, thereby removing salt from the flumetralin.

41. The process of claim 28 further comprising controlling the temperature of the reaction composition during the admixing of said monoethylamine, first alkali, and 2-chloro-6-fluorobenzyl chloride into a first reaction composition to between about −5° C. and about 25° C.

42. The process of claim 28 wherein the reacting of the first reaction composition is at a temperature between about 80° C. and about 100° C.

43. The process of claim 28 wherein the molar ratio of N-ethyl-2-chloro-6-fluoro-benzylamine to 4-chloro-3-5-dinitrobenzotrifluoride in the second reaction composition is between about 0.95:1 to about 1.05:1, and wherein the molar equivalent ratio in the second reaction composition of alkali to 4-chloro-3-5-dinitrobenzotrifluoride is between about 0.95:1 to about 1.05:1.

* * * * *

UNITED STATES PATENT AND TRADEMARK OFFICE
CERTIFICATE OF CORRECTION

PATENT NO. : 6,137,009
DATED : October 24, 2000
INVENTOR(S) : Stefan Kwiatkowski; Steven G. Mobley; Krzysztof Pupek; Miroslaw Golinski; and Paul D. Smith It is certified that error appears in the above-identified patent and that said Letters Patent is hereby corrected as shown below:

In column 4, line 2 the "F" should be deleted and an "H" entered in its place.

Signed and Sealed this

Eighth Day of May, 2001

*Attest:*

NICHOLAS P. GODICI

*Attesting Officer*     Acting Director of the United States Patent and Trademark Office